United States Patent [19]

Barth

[11] Patent Number: 4,814,163

[45] Date of Patent: Mar. 21, 1989

[54] SOLID ANTITARTAR MOUTH DEODORANT

[75] Inventor: Jordan Barth, East Brunswick, N.J.

[73] Assignee: Colgate-Palmolive Company, New York, N.Y.

[21] Appl. No.: 933,968

[22] Filed: Nov. 24, 1986

Related U.S. Application Data

[63] Continuation-in-part of Ser. No. 837,989, Mar. 10, 1986.

[51] Int. Cl.⁴ .................. A61K 7/16; A61K 33/30
[52] U.S. Cl. ...................................... 424/49; 424/145
[58] Field of Search ........................ 424/48, 49, 145

[56] References Cited

U.S. PATENT DOCUMENTS

| | | | |
|---|---|---|---|
| 2,894,876 | 7/1959 | Scanlan et al. | 424/55 |
| 3,228,844 | 1/1966 | Strean | 424/58 |
| 3,556,811 | 1/1971 | Smith | 99/134 |
| 4,022,880 | 5/1972 | Vinson | 424/49 |
| 4,041,149 | 8/1977 | Gaffar et al. | 424/57 |
| 4,082,841 | 4/1978 | Pader | 424/50 |
| 4,100,269 | 7/1978 | Pader | 424/49 |
| 4,138,477 | 2/1978 | Gaffar | 424/52 |
| 4,144,323 | 3/1979 | Lamberti | 424/54 |
| 4,169,885 | 10/1979 | Raaf et al. | 424/49 |
| 4,289,754 | 9/1981 | Dhabhar et al. | 424/52 |
| 4,289,755 | 9/1981 | Dhabhar | 424/52 |
| 4,325,939 | 4/1982 | Shah | 424/55 |
| 4,465,662 | 8/1984 | Sato et al. | 424/54 |
| 4,469,674 | 9/1984 | Shah et al. | 424/52 |
| 4,503,070 | 3/1985 | Eby, III | 514/494 |
| 4,568,540 | 2/1986 | Asano et al. | 424/52 |
| 4,689,214 | 8/1987 | Niles et al. | 424/49 |
| 4,689,214 | 8/1987 | Niles, et al. | 424/49 |

FOREIGN PATENT DOCUMENTS

| | | |
|---|---|---|
| 987597 | 4/1976 | Canada . |
| 2229466 | 12/1972 | Fed. Rep. of Germany . |
| 1311060 | 3/1973 | United Kingdom . |

OTHER PUBLICATIONS

Arctander (1969) Perfume and Flavor Chemicals I Ionones II Methylionones.

Primary Examiner—Shep K. Rose
Attorney, Agent, or Firm—Robert L. Stone; Murray M. Grill

[57] ABSTRACT

A non-cariogenic, long-acting, slow dissolving solid antitartar mouth deodorant having improved taste, and a method of providing extended mouth odor reduction and control of tartar formation comprising a zinc compound which provides zinc, an ionone ketone terpene derivative and a mint flavor, as the essential active ingredients with a gluconate salt and an acidic pH to aid in zinc solubilization, in a sugar-free carrier.

20 Claims, No Drawings

SOLID ANTITARTAR MOUTH DEODORANT

This invention relates to novel solid oral formulations comprising a zinc compound which provides zinc, an ionone ketone terpene derivative and a mint flavor as the active antitartar and deodorant ingredients, having an acid pH and containing a gluconate salt to assist in solubilizing the zinc compound, in a sugar free carrier.

BACKGROUND AND PRIOR ART

The prior art discloses assorted deodorant and anticaries lozenges comprising both a cariogenic sugar carrier or a non-cariogenic polyol carrier, containing assorted active ingredients including copper gluconate, Vitamin B-6, antibacterial agents, peroxydiphosphate salts, and a tranexamic acid/carvone combination as shown in U.S. Pat. No. 2,894,876 (copper gluconate in a sugar base), U.S. Pat. No. 3,228,844 (Vitamin B6 in a sucrose or polyethylene glycol base), U.S. Pat. No. 3,556,811 (antibacterial agent in a hard candy base), U.S. Pat. No. 4,041,149 (peroxydiphosphate in a sugar or sorbitol base), and U.S. Pat. No. 4,465,662 (combination of tranexamic acid and carvone in a glucose or starch/gum arabic base).

U.S. Pat. No. 4,169,885 discloses a filled capsule or tablet wherein the water soluble candy-type based outer shell contains an active antiplaque and/or antitartar agent such as fluoride, fluoro-silicate, zinc compound, phosphate salt or antimicrobial agent.

The prior art also discloses mouth deodorant tablets containing ionone as the sole active deodorant ingredient as shown in British Patent No. 1,311,060 and its counterpart Canadian Patent No. 987,597. However, the ionone is in a sugar carrier, which is cariogenic.

Oral compositions containing zinc compounds in the form of a toothpaste, mouthwash as well as a tablet or lozenge are also disclosed in the prior art as shown in U.S. Pat. Nos. 4,138,477; 4,325,939 and 4,469,674.

The prior art is replete with oral compositions containing zinc salts such as zinc chloride, zinc iodide, zinc fluoride, zinc phenol sulfonate and the like as antiseptic agents, and correctives of oral conditions such as pyorrhea. Zinc chloride has commonly been used in oral formulations for its astringency properties. Zinc phenol sulfonate has been utilized in the prior art dentifrice compositions as an antiplaque and anticalculus agent as well as an odor inhibitor of fermentation and putrefaction which occurs in the oral cavity. Compositions in which these soluble zinc salts have been used have had the disadvantages such as leaving an unpleasant astringent taste in the mouth and/or having short-lived efficacy against tartar build-up and plaque, and as an odor inhibitor.

Sparingly soluble zinc salts such as zinc citrate have been used in dentifrice formulations to prolong the anticalculus and antiplaque effectiveness of the zinc ions due to the slow dissolution of the zinc salts in the saliva as disclosed in U.S. Pat. Nos. 4,100,269 and 4,144,323.

The reaction product of a zinc compound and polymer has been described in U.S. Pat. No. 4,138,477 as a compound which effectively controls mouth odor. Such control can last a few hours, but generally not overnight.

The use of a zinc complex of a specific diketone as an agent for combating tartar and tooth discoloration is also known, as set forth in German Patent No. 2,229,466. Thus, it is apparent that zinc compounds are generally known to have deodorizing properties as well as other properties desirable in oral hygiene.

Combinations of a zinc compound with another active ingredient in anticalculus toothpaste and mouthwash compositions such as with an antibacterial agent is disclosed in U.S. Pat. No. 4,022,880; with an enzyme is disclosed in U.S. Pat. No. 4,082,841; with a fluoride compound is disclosed in U.S. Pat. Nos. 4,289,754; 4,289,755 and 4,469,674.

An oral composition in the form of a lozenge containing zinc salicylate, zinc lactate or zinc gluconate in combination with an ionic fluoride salt in a sugar carrier is disclosed in U.S. Pat. No. 4,469,674.

U.S. Pat. No. 4,503,070 disclosed the method of reducing the duration of the common cold by dissolving a zinc gluconate lozenge in the oral cavity every two wakeful hours for seven days.

However, there is no disclosure of a long lasting non-cariogenic solid antitartar and mouth deodorant containing a combination of a zinc compound, an ionone ketone terpene derivative, a mint flavor and a sodium or potassium gluconate, and having an acidic pH, in a sugar-free carrier.

SUMMARY OF THE INVENTION

The primary object of this invention is to provide a solid dose product having tartar reducing properties, longer lasting breath freshening effects and improved taste properties comprising a zinc compound which provides zinc, an ionone ketone terpene derivative and a mint flavor as the active ingredients, and a gluconate salt such as potassium or sodium gluconate and having an acidic pH to increase zinc solubility which increases and extends its odor and tartar removal properties.

Another object of instant invention is to maximize the effectiveness of the active ingredients by using a solid dose form oral formulation such as a slow dissolving tablet or lozenge.

Still another object of present invention is to provide a convenient solid dose product such as a slow dissolving tablet or lozenge having extended odor removal properties and extended tartar removal properties.

To achieve the foregoing and other objects in accordance with the present invention, as embodied and broadly described herein, the solid antitartar and mouth deodorant product of the invention comprises a non-toxic zinc compound which provides about 0.05-1% zinc, and preferably about 0.10-0.25% zinc ions by weight, and about 0.2-2%, and preferably about 0.5-1.0% by wt. of a high mint flavor containing at least 50% mint ingredients and an ionone ketone terpene derivative and a zinc solubilizing combination of a food grade acidifying agent to provide an acid pH and a gluconate salt such as sodium or potassium gluconate in a non-cariogenic carrier.

More specifically, present invention relates to a slow dissolving tablet or lozenge containing a zinc compound which provides about 0.05-1.0% zinc ions, about 0.001-0.5% of an ionone ketone terpene, a high mint flavor, and about 0.1-0.5% by weight of a gluconate salt, in a sugar-free carrier, having an acid pH of about 4.0-6.5 and preferably 4.5-5.

Prior development, disclosed in copending patent application No. 723,786 filed Apr. 16, 1985, now abandoned and its continuation in part application Ser. No. 836,671, filed March 10, 1986, now U.S. Pat. No. 4,689,214, issued Aug. 25, 1987 has shown that effective mouth odor reducing mouthrinses can be obtained by using the combination of zinc chloride, alpha ionone, and mint flavors. The use of a mouthrinse requires the use of a sink. The short duration of use requires higher active ingredient levels with diminished taste effects. Dentifrices with zinc have been shown to have significant tartar reducing properties, but unfortunately may have serious taste problems.

The present invention consists of solid dose form containing the following active ingredients: a nontoxic zinc compound capable of providing about 0.05-1% zinc, an ionone ketone terpene derivative and a mint flavor, and gluconate salt and having an acidic pH to promote zinc solubilization. The solid dose form has the dual advantage of being useable anywhere and with greater convenience and uses a longer contact time to maximize the effectiveness of the active ingredients. This allows the use of lower active ingredients levels, resulting in improved taste, less mouth drying and affords even greater activity. The product is effective for reducing tartar formation and for long lasting breath deodorant effects. The slow dissolving tablet or lozenge Permits longer contact time in the mouth which maximizes its activity.

The novel tablet or lozenge of instant invention has the dual advantage of being useable anywhere, and provides increased contact time over dentifrice or mouth rinse, to maximize the effectiveness of the active ingredients. This results in improved taste, reduced tartar formation and longer lasting breath deodorancy.

In accordance with the present invention, the zinc compounds that provide zinc for use in combination with ionone may be any physiologically acceptable zinc compound including the water soluble and sparingly water soluble organic and inorganic zinc salts which provide at least about 0.1 mg of zinc ions per ml of water. The water-soluble zinc salts (at least 1% soluble) are preferred, especially the zinc halides and zinc acetate. Among sparingly soluble zinc salts, zinc citrate is preferred. Examples of suitable zinc salts that may be employed include:

| | |
|---|---|
| zinc stearate | zinc fluoride |
| zinc acetate | zinc formate |
| zinc ammonium sulfate | zinc iodide |
| zinc bromide | zinc nitrate |
| zinc chloride | zinc phenol sulfonate |
| zinc chromate | zinc salicylate |
| zinc citrate | zinc sulfate |
| zinc dithionate | zinc gluconate |
| zinc fluosilicate | zinc succinate |
| zinc tartarate | zinc glycerophosphate |

Other zinc salts disclosed in U.S. Pat. No. 4,138,477 having a solubility of at least about 0.01 mg of zinc ions per ml of water are incorporated herein by reference.

The zinc compound is present in amounts which provide about 0.05-1% by weight of zinc, and preferably about 0.1-0.25% of zinc by weight in the solid oral composition.

The solubility of the zinc salt to provide zinc ions may assist as a factor in the activity against odor formation. However, the effect is synergistically improved when an ionone terpene ketone derivative is present.

In addition to zinc provided as ions from water-soluble and sparingly soluble zinc compound, solid transfer of zinc into the oral cavity may occur. Accordingly, substantially water-insoluble zinc compound such as zinc oxide may be employed in accordance with this invention.

It has additionally been found that gluconate salts at an acidic pH assist in the solubilization of the zinc compound, thereby making more zinc ions readily available, to effect sustained odor and tartar removal for longer time periods. A low level of any food grade organic or inorganic acid in sufficient quantity of about 0.01-0.05% by wt., is conveniently used to adjust the pH of the lozenge to an acid pH of about 4.0 to 6.5, and preferably a pH of about 4.5-5. Suitable acids include organic acids such as saccharin acid, citric acid, malic acid, adipic acid, succinic acid, benzoic acid, and the like, and inorganic acids such as phosphoric acid, pyrophosphoric acids, acid sodium phosphate, hydrochloric acid, sulfuric acid and the like. The preferred acids are acid saccharin, benzoic acid and adipic acid in solid form. This acidity is believed to increase the solubility of the zinc components to release a greater amount of the active zinc ions.

The gluconate salt of present invention is preferably potassium and/or sodium gluconate. Sodium gluconate, $HOCH_2(CHOH)_5 COONa$, a readily available gluconate salt, is a water soluble white crystalline solid or powder, having a pleasant sour taste. The tablet or lozenge containing the sodium gluconate is slightly less astringent than the composition containing no sodium gluconate. This is believed to suggest that a water soluble zinc gluconate complex may be formed. The amount of sodium gluconate effective in solubilizing the zinc salt is about 0.1-0.5% and preferably about 0.2% by weight of the formulation.

Another essential active ingredient in present invention is an ionone ketone terpene derivative containing one ketonic carbonyl group. The basic ionone formula is $(CH_3)_3C_6H_6CH=CHCOCH_3$. It is available as alpha-ionone (b.p. 120° C.) and beta-ionone (b.p. 135° C.), both of which are colorless liquids and slightly soluble in water. Other variants of ionone such as gamma-ionone, dihydroionone and alpha-methyl ionone may also be employed. Furthermore, as used herein, the term "an ionone ketone terpene derivative" includes isomeric forms of ionones e.g., irone. It is convenient to employ it in solid oral compositions in amounts of about 0.001-0.5% by weight, and preferably about 0.005-0.1% by weight. Alpha-ionone is preferred and beta-ionone which is equally or more effective but somewhat poorer tasting is also a preferred ionone ingredient. Ionone may be conveniently included as a component added to a flavoring oil such as oil of peppermint, in amounts of 1-10% by weight of said flavoring oil and preferably 1.5 to 2.0% by weight.

In British Patent No. 1,311,060, it was theorized that amelioration of oral malodors by ionone may have occurred due either to an ability to block odor receptor sites in the olfactory epithelium or to lower olfactory thresholds for the compound, and possibly a combination of both. Regardless of the reason for the effect, however, it is not long-lasting. When reduction in breath odor is evaluated after an overnight sleep period, little, if any, reduction is found. On the other hand, when ionone is in combination with a salt which provides zinc ions, there are synergistic effects in countering breath odor for a prolonged period of time, i.e. overnight and up to 12 hours.

Any suitable mint flavoring or sweetening materials may be employed in supplementing the ionone component of the present invention. It is preferable to include the ionone ketone terpene derivatives as an additive to flavoring mint oils. The presence of the flavoring oil improves the taste of the zinc/ionone-containing product. Flavors in accordance with this invention are high mint flavors containing at least 50% by weight and preferably about 75-100%. Mint ingredients include an oil of peppermint, spearmint and mint derivatives such as menthol and carvone. Other flavors such as anethole, spices, wintergreen and herbs can also be included in the flavor composition. Mint flavors such as oil of peppermint, spearmint and menthol are preferred.

In a typical modification of a flavoring oil of high mint content, which contains about 50-100% mint such as peppermint, spearmint and the like, preferably about 75-100% mint including mint derivatives such as menthol and carvone; the non-mint portion may be anethole, spices, wintergreen, herbs and the like. Suitable sweetening agents include sorbitol, sodium cyclamate, sodium saccharin, acetosulfam, N-l-α-aspartyl-l-phenylaniline-methyl ester ("aspartame"), xylitol, chalcone materials. Suitably, flavor and sweetening agent may together comprise from about 0.20 to 2.5% by weight or more of the compositions of the instant invention.

Aqueous solutions and dispersions of control, placebo and various zinc ion-ionone materials can be tested in an in vitro system and in vivo. In the in vitro test, whole human saliva with L-cysteine as substrate is incubated for 3 hours or overnight at 37° C. in an airtight container. After incubation, the headspace volatile sulfur compound ("VSC", the main cause of offensive breath odor) formation is measured by an instrumental GC-flame photometric technique. Since breath odor has been attributed to the presence of VSC's such as hydrogen sulfide, methyl mercaptan and to a lesser extent, dimethyl sulfide, resulting from putrefactive processes occuring in the oral cavity, the in vitro test provides results comparable to in vivo sensory evaluations.

In vivo studies were conducted on 15 to 17 adults (N) to assess the long lasting breath protection obtained with the use of Tablet A containing 0.5% $ZnCl_2$ and 0.5% high mint α-ionone flavor; lozenge B containing 0.5% $ZnCl_2$, 0.665% high mint α-ionone flavor, 0.025% acid saccharin and 0.2% sodium gluconate; and a control placebo tablet and lozenge without Zn but containing 0.5% conventional flavor. Three hours after the tablet or lozenge is dissolved in the mouth, or overnight if the tablet or lozenge is taken before going to bed, a sample of their breath is extracted and measured for breath odor (volatile sulfur compounds) by an instrumental GC-flame photometric technique. The following Table I summarizes the in-vivo test data.

TABLE I

| | N | Initial Mean | Final Mean | % Decrease |
|---|---|---|---|---|
| Mean *Volatile Sulfur Compounds | | | | |
| 3-Hour - Effect | | | | |
| Placebo Lozenge | 17 | 16.34 ± 3.25 | 11.64 ± 3.51 | 28.8 |
| Lozenge B | 17 | 15.46 ± 3.06 | 7.25 ± 2.83 | 53.1 |
| Overnight Effect | | | | |
| Placebo lozenge | 17 | 16.34 ± 3.25 | 14.68 ± 3.45 | 10.2 |
| Lozenge B | 17 | 15.46 ± 3.06 | 7.73 ± 2.27 | 50.0% |
| Tablet A | 15 | 16.4 ± 3.2 | 12.3 ± 4.24 | 25% |
| Placebo Tablet | 15 | 17.3 ± 2.3 | 16.08 ± 2.9 | 7% |

*Parts per billion/cc of mouth air.

This table clearly shows that mouth lozenge B, in accordance with present invention, gives a 50% overnight reduction in breath volatile sulfur compounds. The absolute value of overnight breath volatile sulfur compounds after use of the lozenge is 7.7 ppb/cc with a standard deviation of 2.3, which is markedly below the critical 10 ppb/cc of mouth air level, the threshhold for perception of VSC. Tablet A which does not contain the acid saccharin and sodium gluconate solubilizers is modestly effective in providing long-lasting odor protection compared to the placebo tablet, the difference being significant statistically. Previous studies have shown that at 10 or below ppb/cc of mouth air, the odor is not perceptable by sensory evaluation.

In vivo tests on 12 subjects reported that the test tablets containing zinc salt, ionone and flavor are generally beneficial to the mouth, are effective in removing residual food odors such as garlic or onion, and have lingering extended breath odor effects. Extended breath odor evaluations run by several experienced people in these evaluations opined that the test tablets have effective extended breath odor reduction properties.

While particularly good results in terms of countering breath odor are obtained by simply applying the aqueous solutions or dispersions of the zinc salt-ionone material, it is understood that it is within the broader aspect of the invention to incorporate zinc salt and ionone material into solid oral compositions such as slow dissolving tablets or lozenges which contain a zinc solubilizing combination of a food grade acidifying agent which provides an acidic pH and sodium gluconate in a noncariogenic carrier which is sugar free.

The vehicle or carrier in a tablet or lozenge is a non-cariogenic solid water soluble polyhydric alcohol (polyol) such as mannitol, xylitol, sorbitol, maltitol, a hydrogenated starch hydrolysate ("Lycasin"), hydrogenated glucose, hydrogenated disaccharides and hydrogenated polysaccharides as the major ingredient, in an amount of about 90-98% by weight of the total composition. Solid salts such as sodium bicarbonate, sodium chloride, potassium bicarbonate or potassium chloride may totally or partially replace the polyol carrier.

Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and "carbowax".

Lozenge formulations contain about 2% gum as barrier agent to provide a shiny surface as opposed to a tablet which has a smooth finish. Suitable non-cariogenic gums include kappa carrageenan, carboxymethyl cellulose, hydroxyethyl cellulose, "Gantrez" (poly(-vinylmethyl ethermaleic anhydride)) and the like.

The lozenge or tablet may optionally be coated with a coating material such as waxes, shellac, carboxymethyl cellulose, polyethylene/malic anhydride copolymer or kappa carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose oral composition of this invention affords a longer time period of contact with the active ingredients in the mouth than a toothpaste, toothpowder or mouthrinse which is typically in contact with the mouth for only about 30-90 seconds of brushing or rinsing.

Any suitable or compatible surface-active or detersive material may be incorporated in the solid dental vehicle. Such compatible materials are desirable to provide additional detersive, foaming and antibacterial properties depending upon the specific type of surface-active material and are selected similarly. These detergents are water-soluble organic compounds usually, and may be anionic, nonionic, or cationic in structure. Suitable detersive materials are known and include, for example, the water-soluble salts of higher fatty acid monoglyceride monosulfate detergent (e.g., sodium coconut fatty acid monoglyceride monosulfate), higher alkyl sulfates (e.g., sodium lauryl sulfate), alkyl aryl sulfonate (e.g. sodium dodecyl benzene sulfonate), methylcocoyl taurate, higher fatty acid esters of 1,2-dihydroxypropanesulfonate) and the like.

Further detersive materials include the substantially saturated higher aliphatic acyl amides of lower aliphatic amino carboxylic acid compounds, such as those having 12 to 16 carbons in the acyl radical. The amino acid portion is derived generally from the lower aliphatic saturated monoamino carboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine, N-lauroyl sarcoside, N-lauroyl sarcosine, and sodium N-lauroyl glycine and alanine. For convenience herein, reference to "amino carboxylic acid compound", "sarcoside", and the like refers to such compounds having a free carboxylic group or the water-soluble carboxylate salts.

Other particularly suitable surface-active materials include nonionic agents such as condensates of sorbitan monostearate with approximately 20 moles of ethylene oxide, sorbitan diisostearate condensed with 40 moles of polyethylene glycol, condensates of ethylene oxide with propylene glycol ("Pluronics" PLURONIC is a Trade Mark) and castor oil ester (e.g. Cremopher EL); and amphoteric agents such as quaternized imidazole derivatives, which are available under the trade mark MIRANOL such as MIRANOL C2M. It is preferred to use the nonionic surfactants, particularly the condensates of sorbitan monostearate or diisostearate with 20 to 40 moles of ethylene oxide or polyethylene glycol. Cationic surface active germicides and anti-bacterial compounds such as diisobutylphenoxyethoxyethyl dimethyl benzyl ammonium chloride, tertiary amines having one fatty alkyl group (of from 12–18 carbon atoms) and two (poly)oxyethylene groups attached to the nitrogen (typically containing a total of from 20 to 50 ethanoxy groups per molecule) and salts thereof with acids, and compounds of the structure:

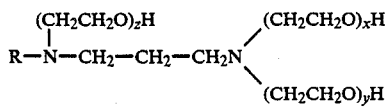

wherein R is a fatty alkyl group typically containing from 12 to 18 carbon atoms, and x, y and z total 3 or higher, as well as salts thereof with mineral or organic acids, may also be used.

The various surface-active materials may be used in any suitable amount, generally from about 0.05 to about 5% by weight, and preferably from about 0.5 to 2% by weight of the solid dentifrice composition.

Antibacterial agents may also be employed in the solid vehicles of the instant invention. Typical antibacterial agents include:

$N^1$-(4-chlorobenzyl)-$N^5$-(2,4dichlorobenzyl) biguanide p-chlorophenyl biguanide;
4-chlorobenzhydryl biguanide;
4-chlorobenzhydrylguanylurea;
N-3-lauroxypropyl-N-p-chlorobenzylbiguanide;
1,6-di-p-chlorophenylbiguanide hexane;
1-(lauryldimethylammonium)-8-(p-chlorobenzyl dimethyl ammonium) octane dichloride;
5,6-dichloro-2-guanidinobenzimidazole;
N'-p-chlorophenyl-$N^5$-laurylbiguanide;
5-amino-1,3-bis(2-ethylhexyl)-3-methylhexahydro pyrimidine;
and their non-toxic acid addition salts.

Minor amounts of coloring agents, dyes or ultraviolet absorbers to enhance the color, and the like so as to improve the aesthetic value and consumer acceptability, may also be included in the tablets and lozenges of present invention.

The tablets and lozenges of present invention are prepared by methods of dry mixing or blending the ingredients with an inert carrier, or dissolving in a suitable carrier. The blended mixture is introduced into a tablet machine to shape the final product.

The solid dose oral preparations are slowly dissolved in the mouth for a period of about 3 to 5 minutes, which affords long lasting breath deodorancy up to about 12 hours duration.

DETAILED DESCRIPTION OF THE INVENTION

The following specific examples are further illustrative of the present invention, but it is understood that the invention is not limited thereto. All amounts of various ingredients are by weight unless otherwise specified.

| | Tablets Examples 1-3 | | |
|---|---|---|---|
| | Parts | | |
| Ingredients | 1 | 2 | 3 |
| Sorbitol (Powdered) | 95.329 | 93.250 | 95.8665 |
| Sodium Saccharin | 0.275 | 0.450 | 0.150 |
| Acid Saccharin | 0.025 | 0.03 | 0.025 |
| Coconut Oil | 2.000 | 3.000 | 2.000 |
| Sodium gluconate | 0.2 | 0.30 | 0.20 |
| PEG-40 Sorbitan Diisostearate | 1.000 | 1.500 | 1.000 |
| Blue Dye | 0.006 | 0.010 | 0.006 |
| Zinc Chloride | 0.500 | 0.750 | 0.500 |
| High Mint (85-95%) Flavor | 0.655 | 1.20 | 0.250 |
| Alpha Ionone | 0.01 | 0.010 | 0.0025 |
| pH is about 5. | | | |

Preparation of Examples at Room Temperature

Zinc chloride is preblended with approximately 5% of the formula amount of powdered sorbitol, and subsequently mixed with the remainder of the sorbitol in a suitable blender until thoroughly dispersed. The sodium saccharin, acid saccharine and sodium gluconate are added to, and mixed with, the zinc-sorbitol mixture. The diisostearate surfactant is preblended with the mint flavor, α-ionone and dye and said preblend is added to the mixture in the blender and mixed thoroughly. The coconut oil is added to the formulation in the blender and thoroughly mixed. The formula is introduced into a tableting machine such as a rotary tablet press to shape the final product. The final product is a white tablet with blue speckles, having a smooth finish, each tablet weighing 1½ grams. These tablets exhibit extended mouth odor reduction properties and provide substantial reduction in tartar formation. Each dissolves slowly in the mouth, in about 3 to 5 minutes. These tablets counter breath odors overnight and up to 12 hours after total dissolution in the mouth.

EXAMPLE 4

Example 1 is repeated except that 0.4% magnesium stearate is substituted for the coconut oil and the sorbitol content is increased to 96.929. This product also yields blue speckled, white tablets having the same unexpected long-lasting breath deodorant and tartar reducing properties as stated above.

EXAMPLE 5

Example 1 is repeated except that mannitol is substituted for the sorbitol carrier, yielding a tablet substantially as effective as in Example 1.

EXAMPLE 6

Example 2 is repeated except that Lycasin is substituted for the sorbitol carrier. Lycasin, developed by Roquette Freres, *The Manufacturing Confectioner*, December 1983, pp. 69-74, is a hydrogenated starch hydrolysate which is a bright, colorless syrup having a viscosity of about 2,000 cps at 20° C., comprising 75% dry substances which include 6 to 8% D-sorbitol, 50 to 55% hydrogenated disaccharides, 20 to 25% tri- to hexasaccharides, and 15-20% hydrogenated saccharides higher than hexa.

EXAMPLE 7

Example 1 is repeated except that sodium bicarbonate is substituted for the sorbitol carrier yielding tablets capable of countering breath odors and tartar formation over a protracted period of time.

EXAMPLE 8

Example 2 is repeated, but zinc citrate is substituted for the zinc chloride as the source of the zinc ions. The final product is substantially as effective as the tablets of Example 2.

EXAMPLE 9

Example 2 is repeated, but zinc stearate is substituted for the zinc chloride as the source of zinc ions. The final product is substantially as effective as the tablets of Example 2.

EXAMPLE 10

Example 1 is repeated, but zinc oxide is substituted for the zinc compounds as the transfer source of zinc. The final product is substantially as effective as the tablets of Example 1.

EXAMPLE 11

| Ingredients | Lozenge Parts |
|---|---|
| Kappa Carrageenan | 2.0 |
| Sorbitol (Powdered) | 93.329 |
| Sodium Saccharin | 0.275 |
| Acid Saccharin | 0.025 |
| Coconut Oil | 2.00 |
| Sodium gluconate | 0.2 |
| PEG-40 Sorbitan Diisostearate | 1.00 |
| Blue Dye | 0.006 |
| Zinc Chloride | 0.500 |
| High Mint (85-95%) Flavor | 0.655 |
| Alpha Ionone | .01 |
| pH is about 5 | |

The sorbitol is thoroughly blended with the kappa carrageenan. Zinc chloride, sodium saccharin, acid saccharin and sodium gluconate are added to, and mixed with, the sorbitol/carrageenan blend to form a powder blend. The dye is dispersed in the diisostearate surfactant and added to the powder blend followed by the addition of coconut oil. The total mixture is heated to about 240° F. with mixing. The mixture is cooled to 180° F. and the flavor including ionone is added. The cooled mixture is molded, stored until hard and demolded. The resulting product is a long-acting breath odor control lozenge. It is not merely a candy mint, which temporarily masks odors, nor is it a medicine-type or mint-type liquid with which one washes the oral cavity. It is a new slow dissolving lozenge with a special combination of zinc and an ionone as long lasting odor controllers, with the combination of an acidifying agent providing an acid pH and a gluconate salt to aid in zinc solubilization to extend mouth odor reduction and control tartar formation. Thus it can conveniently be used after meals; at bedtime; essentially any time and anywhere. As the lozenge dissolves, the effective odor fighting ingredients work with saliva to form an odor controlling system that keeps working even after the next meal. Taken after bedtime, its effect lasts overnight to counter morning mouth odor. It provides long lasting mouth refreshment. The lozenge additionally controls tartar build-up throughout the day by forming a long acting, protective barrier of the combination of active ingredients, zinc ions and ionone, to give a cleaner, hygienic mouth.

Other ionone ketone terpene derivatives can replace the alpha-ionone in the Examples, such as beta-ionone, dihydroionone and alpha-methyl ionone. Similarly, other sweeteners can replace the sodium saccharin such as sodium cyclamate, chalcone materials etc. Also, other high mint flavors can replace the peppermint oil such as spearmint oil and the like. Likewise, other surfactants can replace the PEG-40 Sorbitan diisostearate such as polyoxyethylene (20) sorbitan monoisostearate and the "Pluronics".

Although this invention has been described with reference to specific examples, it is understood that modifications and variations of compositions and procedure are contemplated within the scope of the following claims.

What is claimed:

1. A slow dissolving solid antitartar and mouth deodorant composition comprising a physiologically acceptable zinc compound selected from the group consisting of water-soluble zinc salts, sparingly water-soluble zinc salts and water-insoluble zinc salts, which provides about 0.05 to 1% by weight of zinc ions, about 0.2 to 2% by weight of a high mint flavor containing at least 50% mint ingredients selected from the group consisting of oil of peppermint, oil of spearmint, and carvone; and an ionic ketone terpene derivative selected from the group consisting of alpha-ionone, beta-ionone, gamma ionone, dihydroionone, alpha-methylionone and irone; and a zinc solubilizing combination of about 0.1-0.5% by weight of a sodium of potassium gluconate salt and a food grade acidifying agent to provide an acidic pH of about 4.0-6.5, in a non-cariogenic solid carrier selected from the group consisting of a water soluble polyhydric alcohol, hydrogenated starch hydrolysate, hydrogenated glucose, hydrogenated disaccharide; hydrogenated polysaccharide, sodium or potassium bicarbonate, sodium or potassium chloride, and mixtures thereof.

2. The solid composition according to claim 1, which is in the form of a sugar-free dissolving tablet or lozenge.

3. The composition according to claim 2 wherein the ionone ketone terpene derivative is present in amounts of about 0.001-0.5% by weight.

4. The composition according to claim 2 wherein said ionone ketone terpene derivative is alpha-ionone.

5. The composition according to claim 1 wherein said zinc compound is water-soluble or sparingly soluble and provides at least 0.1 mg of zinc ions in 1 ml of water.

6. The composition according to claim 5 wherein said zinc compound is zinc stearate.

7. The composition according to claim 5 wherein said zinc compound is zinc chloride.

8. The composition according to claim 5 wherein said zinc composition is zinc citrate.

9. The composition according to claim 1 wherein said zinc compound is zinc oxide.

10. The composition according to claim 1 wherein said carrier is a sugar free water soluble polyhydric alcohol, in an amount of about 90-98% by weight of the composition.

11. The composition according to claim 1, wherein said solid carrier is a sugar-free sodium bicarbonate salt in an amount of about 90-98% by weight of the composition.

12. The composition according to claim 3 wherein said ionone ketone terpene derivative is present as a component of a flavoring oil in amounts of about 1-10% by weight of said flavoring oil.

13. A method of providing extended mouth odor reduction and to control tartar formation which comprises essentially of introducing in the oral cavity a slow dissolving tablet or lozenge comprising a physiologicaly acceptable zinc compound selected from the group consisting of water-soluble zinc salts, sparingly water-soluble zinc salts and water-insoluble zinc salts, which provides about 0.05-1% by weight of zinc, and about 0.001-0.5% by weight of an ionone ketone terpene derivative selected from the group consisting of alpha-ionone, beta-ionone, gamma-ionone, dihydroionone, alpha-methylionone and irone, and about 0.2-2% by weight of a high mint flavor containing at least 50% mint ingredients selected from the group consisting of oil of peppermint, oil of spearmint, menthol and carvone, and a zinc solubilizing combination of about 0.01-0.05% by weight of a food grade organic or iorganic acid to adjust the pH of the composition to an acid pH of about 4.0-6.5, and 0.1-0.5% by weight sodium or potassium gluconate, in a solid sugar-free carrier selected from the group consisting of a water soluble polyhydric alcohol, hydrogenated starch hydrolysate, hydrogenated glucose, hydrogenated disaccharide, hydrogenated polysaccharide, sodium or potassium bicarbonate, sodium or potassium chloride, and mixtures thereof.

14. The method of countering breath odor according to claim 13 wherein said ionone ketone terpene derivative is alpha-ionone and said zinc salt is zinc chloride.

15. The composition according to claim 10, wherein the water soluble polyhydric alcohol is sorbitol.

16. The composition according to claim 10, wherein the water soluble polyhydric alcohol is mannitol.

17. The composition according to claim 1, wherein said solid carrier is a hydrogenated starch hydrolysate in an amount of about 90-98% by weight of the composition.

18. A composition according to claim 1, wherein the acidifying agent is a food grade organic or inorganic acid in a sufficient amount of about 0.01-0.05% by weight to adjust the pH to about 4.0-6.5.

19. The composition according to claim 18, wherein the organic acid is a solid organic acid selected from the group consisting of saccharin acid, adipic acid and benzoic acid.

20. The solid composition according to claim 2, wherein the zinc compound is zinc chloride, the ionone is alpha-ionone, the flavor contains 85-95% mint ingredients, and the acidifying agent is saccharin acid in a water soluble polyhydric alcohol solid carrier.

* * * * *